United States Patent
Ash et al.

(10) Patent No.: US 8,029,457 B2
(45) Date of Patent: Oct. 4, 2011

(54) INDWELLING CATHETER WITH ANTI-CLOTTING FEATURES

(75) Inventors: Stephen R. Ash, Lafayette, IN (US); Kenneth E. Brown, West Lafayette, IN (US)

(73) Assignee: AAT Catheter Technologies, LLC, Lafayette, IN (US)

( * ) Notice: Subject to any disclaimer, the term of this patent is extended or adjusted under 35 U.S.C. 154(b) by 109 days.

(21) Appl. No.: 11/528,733

(22) Filed: Sep. 27, 2006

(65) Prior Publication Data

US 2007/0225661 A1    Sep. 27, 2007

Related U.S. Application Data (63) Continuation-in-part of application No. 11/388,726, filed on Mar. 24, 2006.

(60) Provisional application No. 60/819,927, filed on Jul. 11, 2006.

(51) Int. Cl.
*A61M 3/00* (2006.01)
*A61M 5/178* (2006.01)
*A61M 5/32* (2006.01)
*A61M 1/00* (2006.01)
*A61M 25/00* (2006.01)

(52) U.S. Cl. ........... 604/43; 604/164.02; 604/167.01; 604/266; 604/27; 604/284; 604/523; 604/524; 604/525; 604/526

(58) Field of Classification Search .......... 604/264, 604/284, 523, 524, 525, 526, 93.01, 27, 43, 604/48, 266, 268, 164.01, 164.02, 167.01
See application file for complete search history.

(56) References Cited

U.S. PATENT DOCUMENTS

| | | | |
|---|---|---|---|
| 396,754 A | | 1/1889 | Mayfield |
| 2,649,092 A | | 8/1953 | Wallace |
| 3,108,595 A | | 10/1963 | Overment |
| 3,397,699 A | * | 8/1968 | Kohl ............... 604/105 |
| 3,841,308 A | * | 10/1974 | Tate ................ 600/585 |
| 3,938,530 A | | 2/1976 | Santomieri |
| 4,256,102 A | | 3/1981 | Monaco |
| 4,327,722 A | | 5/1982 | Groshong et al. |
| 4,368,737 A | | 1/1983 | Ash |
| 4,549,879 A | | 10/1985 | Groshong et al. |
| 4,619,643 A | | 10/1986 | Bai |
| 4,657,536 A | | 4/1987 | Dorman |
| 4,687,471 A | | 8/1987 | Twardowski et al. |
| 4,701,166 A | | 10/1987 | Groshong et al. |
| 4,772,268 A | | 9/1988 | Bates |

(Continued)

FOREIGN PATENT DOCUMENTS

EP    0 348 136 A2    12/1989

(Continued)

OTHER PUBLICATIONS

Supplementary European Search Report. PCT/US2007015283 Jan. 20, 2011. Ash Access Technology, Inc.

*Primary Examiner* — Theodore Stigell
*Assistant Examiner* — Shefali Patel
(74) *Attorney, Agent, or Firm* — Kreig DeVault, LLP (57) ABSTRACT

A catheter for providing blood flow includes first and second lumen parts having a distal portion with at least one port for delivering and receiving flow from a patient and a non-linear profile along the distal portion.

15 Claims, 7 Drawing Sheets

U.S. PATENT DOCUMENTS

| | | | |
|---|---|---|---|
| 4,822,345 | A | 4/1989 | Danforth |
| 4,854,322 | A | 8/1989 | Ash et al. |
| 4,895,561 | A | 1/1990 | Mahurkar |
| 4,935,004 | A | 6/1990 | Cruz |
| 4,973,319 | A | 11/1990 | Melsky |
| 5,053,023 | A | 10/1991 | Martin |
| 5,057,075 | A | 10/1991 | Moncrief et al. |
| 5,156,592 | A | 10/1992 | Martin et al. |
| 5,163,921 | A | 11/1992 | Feiring |
| 5,209,723 | A | 5/1993 | Twardowski et al. |
| 5,221,255 | A | 6/1993 | Mahurkar et al. |
| 5,221,256 | A | 6/1993 | Mahurkar |
| 5,250,034 | A | 10/1993 | Appling et al. |
| 5,261,885 | A | 11/1993 | Lui |
| 5,304,155 | A | 4/1994 | Lui |
| 5,322,519 | A | 6/1994 | Ash |
| 5,360,397 | A | 11/1994 | Pinchuk |
| 5,374,245 | A * | 12/1994 | Mahurkar ............ 604/43 |
| 5,380,276 | A | 1/1995 | Miller et al. |
| 5,395,353 | A | 3/1995 | Scribner |
| 5,403,291 | A | 4/1995 | Abrahamson |
| 5,405,320 | A | 4/1995 | Twardowski et al. |
| 5,489,278 | A | 2/1996 | Abrahamson |
| 5,509,897 | A | 4/1996 | Twardowski et al. |
| 5,527,330 | A * | 6/1996 | Tovey ............ 606/167 |
| 5,533,980 | A * | 7/1996 | Sweeney et al. ............ 604/192 |
| 5,542,937 | A * | 8/1996 | Chee et al. ............ 604/523 |
| 5,569,182 | A | 10/1996 | Twardowski et al. |
| 5,674,197 | A | 10/1997 | Van Muiden et al. |
| 5,702,365 | A | 12/1997 | King |
| 5,733,248 | A | 3/1998 | Adams et al. |
| 5,776,096 | A | 7/1998 | Fields |
| 5,776,111 | A | 7/1998 | Tesio |
| 5,807,311 | A | 9/1998 | Palestrant |
| 5,807,339 | A | 9/1998 | Bostrom et al. |
| 5,807,349 | A | 9/1998 | Person et al. |
| 5,827,305 | A * | 10/1998 | Gordon ............ 606/159 |
| 5,961,486 | A | 10/1999 | Twardowski et al. |
| 6,001,079 | A | 12/1999 | Pourchez |
| 6,110,164 | A | 8/2000 | Vidlund |
| 6,113,568 | A | 9/2000 | Olaussen |
| 6,190,349 | B1 * | 2/2001 | Ash et al. ............ 604/43 |
| 6,270,489 | B1 * | 8/2001 | Wise et al. ............ 604/508 |
| 6,315,757 | B1 * | 11/2001 | Chee et al. ............ 604/103.09 |
| 6,364,867 | B2 | 4/2002 | Wise et al. |
| 6,409,699 | B1 | 6/2002 | Ash |
| 6,482,169 | B1 | 11/2002 | Kuhle |
| 6,547,761 | B2 | 4/2003 | Liu |
| 6,569,150 | B2 | 5/2003 | Teague et al. |
| 6,579,261 | B1 | 6/2003 | Kawamura |
| 6,585,681 | B2 | 7/2003 | Brugger et al. |
| 6,638,242 | B2 | 10/2003 | Wilson et al. |
| 6,719,749 | B1 | 4/2004 | Schweikert et al. |
| 6,749,580 | B2 | 6/2004 | Work et al. |
| 6,814,718 | B2 | 11/2004 | McGuckin, Jr. et al. |
| 6,858,019 | B2 | 2/2005 | McGuckin, Jr. et al. |
| 6,872,198 | B1 | 3/2005 | Wilson et al. |
| 6,911,014 | B2 | 6/2005 | Wentling et al. |
| 6,916,313 | B2 * | 7/2005 | Cunningham ............ 604/533 |
| 6,976,973 | B1 | 12/2005 | Ruddell et al. |
| 6,997,894 | B2 | 2/2006 | Caresio |
| 7,013,928 | B2 | 3/2006 | Navis |
| 7,108,674 | B2 | 9/2006 | Quinn |
| RE39,451 | E | 12/2006 | Kuhle |
| 7,465,286 | B2 * | 12/2008 | Patterson et al. ............ 604/43 |
| 2001/0023333 | A1 | 9/2001 | Wise et al. |
| 2002/0016584 | A1 | 2/2002 | Wise et al. |
| 2002/0143292 | A1 | 10/2002 | Flinchbaugh |
| 2003/0158538 | A1 * | 8/2003 | Deniega et al. ............ 604/523 |
| 2003/0191450 | A1 | 10/2003 | Teague et al. |
| 2003/0204162 | A1 | 10/2003 | Childers et al. |
| 2004/0167463 | A1 | 8/2004 | Zawacki et al. |
| 2005/0038413 | A1 | 2/2005 | Sansoucy |
| 2005/0096609 | A1 | 5/2005 | Maginot et al. |
| 2005/0101941 | A1 | 5/2005 | Hakky et al. |
| 2005/0177105 | A1 | 8/2005 | Shalev |
| 2005/0245900 | A1 | 11/2005 | Ash |
| 2005/0277862 | A1 * | 12/2005 | Anand ............ 604/4.01 |
| 2006/0020256 | A1 | 1/2006 | Bell et al. |
| 2006/0161118 | A1 | 7/2006 | Maginot et al. |
| 2007/0225682 | A1 | 9/2007 | Ash et al. |

FOREIGN PATENT DOCUMENTS

| | | |
|---|---|---|
| EP | 0 931 559 A2 | 7/1999 |
| WO | WO 94/09845 | 5/1994 |
| WO | WO 2005/025645 | 3/2005 |

* cited by examiner

INDWELLING CATHETER WITH ANTI-CLOTTING FEATURES

CROSS-REFERENCE TO RELATED APPLICATIONS

This application claims the benefit of the filing date of U.S. Provisional Patent Application No. 60/819,927 filed on Jul. 11, 2006, which is incorporated herein by reference in its entirety. The present application is also a continuation-in-part of U.S. patent application Ser. No. 11/388,726 filed on Mar. 24, 2006, which is also incorporated herein by reference in its entirety.

BACKGROUND

Patients with end stage renal disease (ESRD) must routinely receive dialysis treatments in order to live. Indwelling catheters are a useful dialysis access method for hemodialysis because they reduce the number of vein penetrations needed for repeated dialysis. Chronic central venous catheters for dialysis (CVCD) are the major long-term dialysis access for over 25% of ERSD patients or hemodialysis.

In a standard flow-through dialysis system, the CVCD must provide a first route for removal of blood and a second route for return of blood at a rate of at least 300 ml/min. A CVCD for a standard flow-through dialysis system can be formed by inserting two separate catheters into the jugular vein in a manner that forms a tunnel over the clavicle. In this arrangement, the catheter tips rest near the junction of the superior vena cava with the right atrium. The tip of the blood removal catheter, or arterial catheter, is placed 3-4 cm above the tip of the downstream blood return catheter, or venous catheter, in order to prevent mixture of cleansed blood with blood entering the arterial catheter.

As an alternative to the separate catheter for the standard flow-through dialysis system, a single-bodied catheter with two separate lumens can be used for dialysis access. In this arrangement, the tip of the arterial lumen is placed 3-4 cm above the tip of the venous lumen. Like the standard flow-through arrangement, this arrangement also prevents mixture of cleansed blood with blood entering the arterial lumen. As yet another alternative, dialysis can also be performed by using a single catheter with a single lumen. In this case, the dialysis machine delivers a quantity of untreated blood and then returns treated blood in alternating cycles.

Blood enters and exits the catheter lumen through ports or holes in the catheter. The design of these ports is highly variable, and similar concepts are employed in both single and dual lumen catheters. A first example is a catheter lumen having a single port at the tip for entrance or exit of blood. A second example is a catheter lumen having a blood exchange port located on the side of the lumen body toward its distal tip. Another example is a catheter lumen having multiple blood exchange ports axially placed around the side of the lumen body toward its distal tip. While all of the above CVCD designs work, there is room for improvement in the field, and there are problems with all current port designs for dialysis catheters.

Arterial catheter lumens that contain only one blood exchange port, no matter its location, run the risk of obstruction of the port by neighboring vein walls, by blood clotting in the exchange port, and by growth of a fibrin sheath around the distal end of the lumen and exchange port. Venous catheter lumens that contain only one blood exchange port, no matter its location, run the risk of obstruction by blood clotting in the exchange port and by growth of a fibrin sheath around the distal end of the lumen and the exchange port. Obstruction of the blood exchange port prevents the desired blood exchange rate of at least 300 ml/min from occurring. The degree of obstruction may render the indwelling catheter(s) ineffective for dialysis access. Therefore, when this level of obstruction occurs, the indwelling catheter(s) must be replaced.

Arterial catheter lumens containing multiple blood exchange ports around the distal end of the catheter reduce the occurrence of vein obstruction. However, the presence of multiple ports increases the risk of obstruction by blood clots because the multiple ports allow blood to flow into the lumen when idle, which can wash out the anticoagulant solution. The diminished presence of anticoagulant solution at the distal end of the catheter increases the amount of blood clotting in the ports and lumen. Obstruction of the blood exchange ports prevents the desired blood exchange rate of at least 300 ml/min from occurring. The degree of obstruction may render the indwelling catheter(s) ineffective for dialysis access. Therefore, when this level of obstruction occurs, the indwelling catheter(s) must be replaced.

Thus, there is a general need in the industry to provide methods and devices for the prevention of obstructions in the blood exchange ports of catheters and around the distal end of catheters. It is desired that these methods and devices prevent obstructions of the lumen due to clotting and fibrous sheath encasement of the tip of the catheter, as well as maintain the catheter anti-coagulant lock solution inside the lumen during idle periods between dialysis.

SUMMARY

The present invention is directed to an indwelling catheter. More particularly, but not exclusively, one aspect relates to an indwelling catheter adapted to prevent clotting and sheathing of the catheter's distal end. One application of the catheter includes non-exclusive use as a catheter for dialysis (CVCD). Other applications are also contemplated.

In one aspect, a catheter includes an elongate body that includes a pair of lumen parts each having a lumen or passage for fluid flow therethrough. Each of the lumen parts extends between a distal and a proximal end and includes a port at or adjacent the distal end thereof in communication with the lumen.

In a further aspect, along the distal portion of the lumen parts, the lumen parts separate from one another. At least one of the lumen parts extends transversely to the longitudinal axis in a non-linear configuration. In another embodiment, each of the lumen parts extends transversely to and forms a non-linear profile relative to the longitudinal axis.

In one embodiment, the catheter also includes a pair of end caps and distally opening distal ports at the distal ends of respective ones of the lumen parts and an actuating mechanism at the proximal end of the catheter. Each of the end caps are coupled to the actuating mechanism with at least one actuating member extending in a wall along the respective lumen. The actuating mechanism is operable to independently and remotely move each of the end caps with the respective actuating member toward and away from the port of the respective lumen part between closed and open positions to permit fluid flow through the respective port.

In another embodiment, the lumen parts each includes a distally opening distal end port in the distal end thereof, and no end caps or valve structure is provided to close the distal end ports.

These and other aspects are further discussed below.

DESCRIPTION OF THE ILLUSTRATED EMBODIMENTS

For the purposes of promoting an understanding of the principles of the inventions, reference will now be made to the embodiments illustrated in the drawings and specific language will be used to describe the same. It will nevertheless be understood that no limitation of the scope of the inventions is thereby intended. Any alterations and further modifications of the principles of the inventions as illustrated or described herein are contemplated as would normally occur to one skilled in the art to which the inventions relate.

The present invention provides a catheter with a non-linear configuration at least along a distal portion thereof that is implanted in a vascular structure of the patient. Applications of the catheter include those requiring long-term vascular access procedures, including hemodialysis and apheresis. Applications in short-term procedures are also contemplated. The catheters are inserted percutaneously into the vascular system. The first and second lumen parts can provide flow out of and into the body. As used herein, flow into the body is also referred to as "venous" flow, and flow out of the body is called "arterial" flow.

The non-linear distal portion includes first and second lumen parts that each includes at least one port to permit fluid flow therethrough. The non-linear configuration improves delivery and return of the fluid from the vascular structure and assists to prevent the formation of a fibrous sheath that could impede catheter performance around the distal catheter portion and the at least one port.

In one embodiment, the at least one port can be provided with a mechanism that allows opening and closing thereof. The at least one port will be in the closed position between dialysis procedures to prevent blood from flowing through the port and to prevent clotting within the tip of the catheter. With the at least one port closed, anticoagulant solution injected in the lumen parts is retained within the catheter lumens.

The catheter can be made from any suitable bio-compatible material, including silicone, polyurethane, polyurethane-polycarbonate copolymer, or any other plastic or polymer material. The catheter can also include an antibacterial coating. The catheter can also be treated with an anti-infection agent, such as methylene blue, for example. The catheter can be of any suitable size for placement in a vessel structure, including sizes ranging from 8 to 15 French. Other sizes are also contemplated. The outer wall surface of the catheter or of the lumen parts forming the catheter can be cylindrical, D-shaped, double D-shaped, or split, for example. The lumen parts can also include a single lumen or multiple lumens extending within the wall of the lumen part. Multiple lumen parts can be fixed to one another along the length of the catheter. In one embodiment, lumen parts are fixed along a substantial portion of the length to a bifurcation in the lumen parts that is fixed in location between a proximal and distal portion of the catheter. In another embodiment, the lumen parts are splittable to vary the location of the bifurcation along the length of the catheter.

Figure 1:
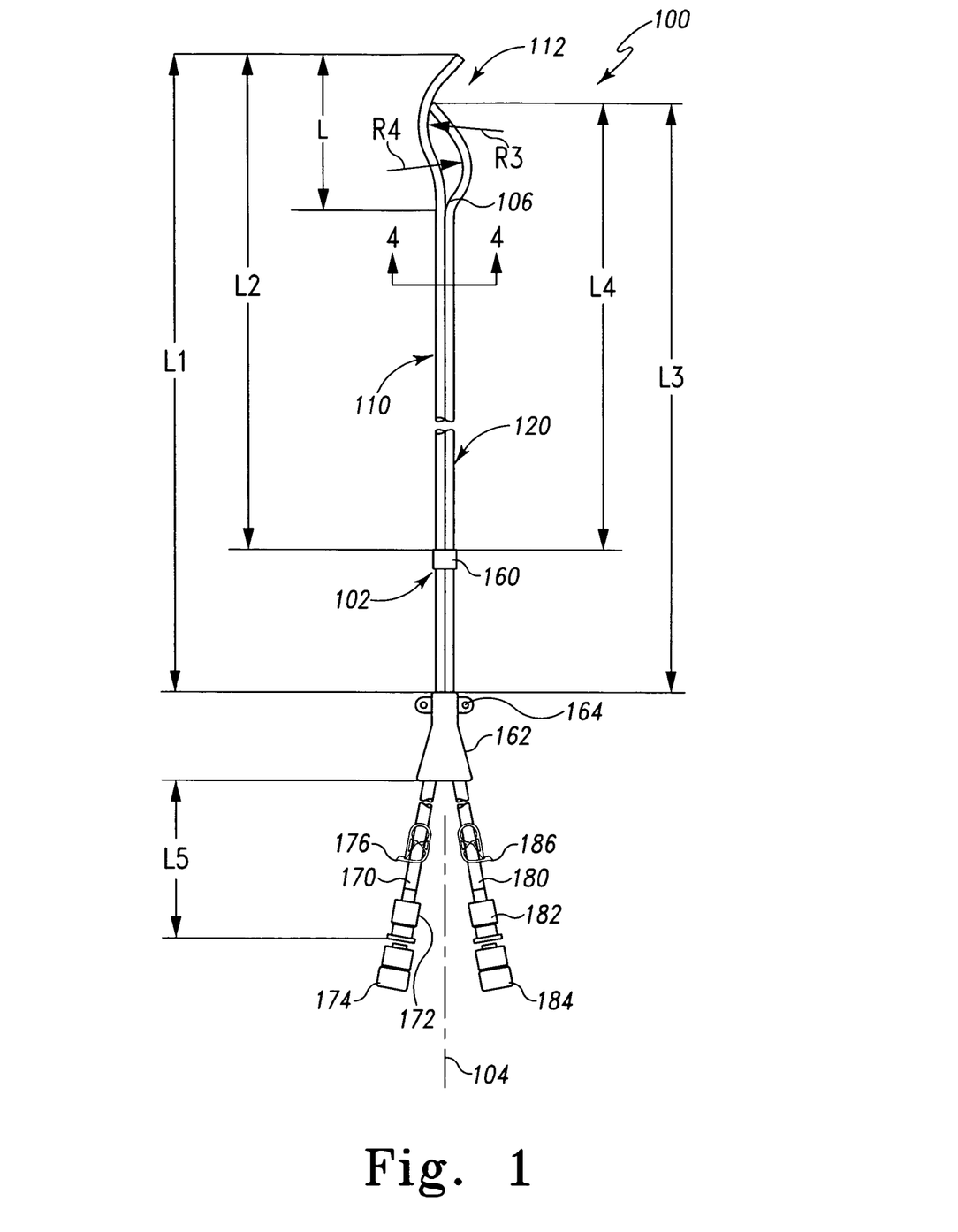
FIG. 1 is a plan view of one embodiment catheter.
Figure 2:
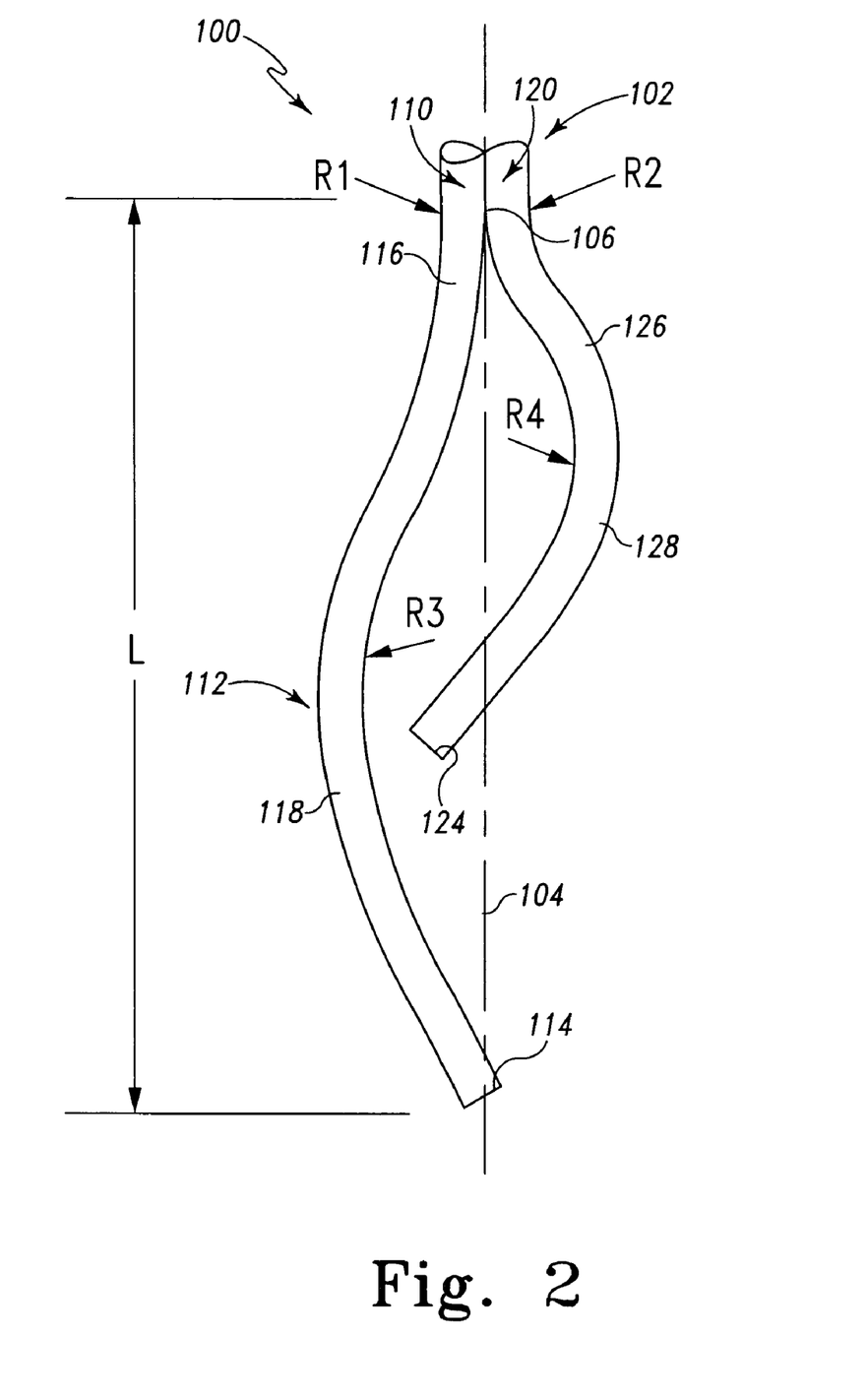
FIG. 2 is a plan view of a distal portion of the catheter of FIG. 1 enlarged relative to FIG. 1.

Referring to FIG. 1, there is shown a catheter 100 having an elongated body that includes lumen parts 110, 120 that can be coupled together or positioned alongside one another along a proximal portion 102. Proximal portion 102 can extend distally and proximally along a longitudinal axis 104. As also shown in FIG. 2, at a distal end of catheter 100 lumen parts 110, 120 form a bifurcation 106 that forms a general Y-shape that separates the two lumen parts 110, 120. The separated lumen parts 110, 120 extend for a length L along longitudinal axis 104 for placement in a vascular structure of the patient. In one embodiment, one of the lumen parts 110, 120 can be designated to provide fluid flow to the body of the patient and the other lumen part 110, 120 can be designated to receive fluid flow from the body of the patient. For example, lumen part 110 can provide venous flow and lumen part 120 can provide arterial flow.

Catheter 100 includes a distal end portion 112 extending distally from bifurcation 106 along axial length L. Length L can be about 6 centimeters, or other suitable length. Distal end portion 112 has a non-linear profile along longitudinal axis 104. In the illustrated embodiment, distal portion 112 forms a double bend configuration to make it less likely that the distal end portion 112 can be encased in a fibrous sheath formed by the patient's body. For example, lumen part 110 forms a first portion 116 that extends from bifurcation 106 along a bend defined by a radius R1. Lumen part 120 forms a first portion 126 that extends from bifurcation 106 along a bend that is defined by radius R2. Radius R1 and radius R2 are located on the side of the respective lumen part 110, 120 away from longitudinal axis 104 so that the lumen parts 110, 120 separate and diverge distally away from longitudinal axis 104 and form a convex relationship toward longitudinal axis 104. Radius R1 and radius R2 can be the same, or can differ from one another.

Lumen part 110 also includes a second portion 118 forming a reverse compound curve-like shape with first portion 116. Second portion 118 extends along a bend defined by a radius R3 to a distal tip 114. Lumen part 120 also includes a second portion 128 that forms a reverse compound curve-like shape with first portion 126. Second portion 128 extends along a bend defined by a radius R4 to a distal tip 124. Radius R3 and radius R4 are located toward longitudinal axis 104 so that the second portions 118, 128 are curved away from longitudinal axis 104 and form a concave relationship oriented toward longitudinal axis 104.

The length of portion 128 along axis 104 is less than the length of portion 118 along axis 104 so that the distal tip 124 is spaced proximally of the distal tip 114. The length of second portion 118 and radius R3 is sized so that second portion 118 crosses longitudinal axis 104 from the first side to the second side of longitudinal axis 104 in a transverse relationship to longitudinal axis 104, and distal tip is located at least partially on the second side of longitudinal axis 104. The length of second portion 128 and radius R4 is sized so that second portion 128 crosses longitudinal axis 1004 from the second side to the first side of axis 104 in a transverse relationship to longitudinal axis 104, and distal tip 124 is located at least partially on the first side of longitudinal axis 104. The radii R1, R2, R3, and R4 are provided as examples of the curvature of the bends of the lumen parts 110, 120. Each portion of the lumen parts 110, 120 can extend along bends formed by multiple radii and that are regular or irregular in form. In another form, the bends include one or more linear or angular segments.

The double bend configuration of distal portion 112 provides a non-linear profile that assists in preventing the formation of a fibrous sheath encasing distal portion 112 when positioned in the patient's body. The diverging and converging relationship between lumen parts 110, 112 provides a non-linear profile for the lumen parts 110, 120 along distal portion 112.

Figure 3:
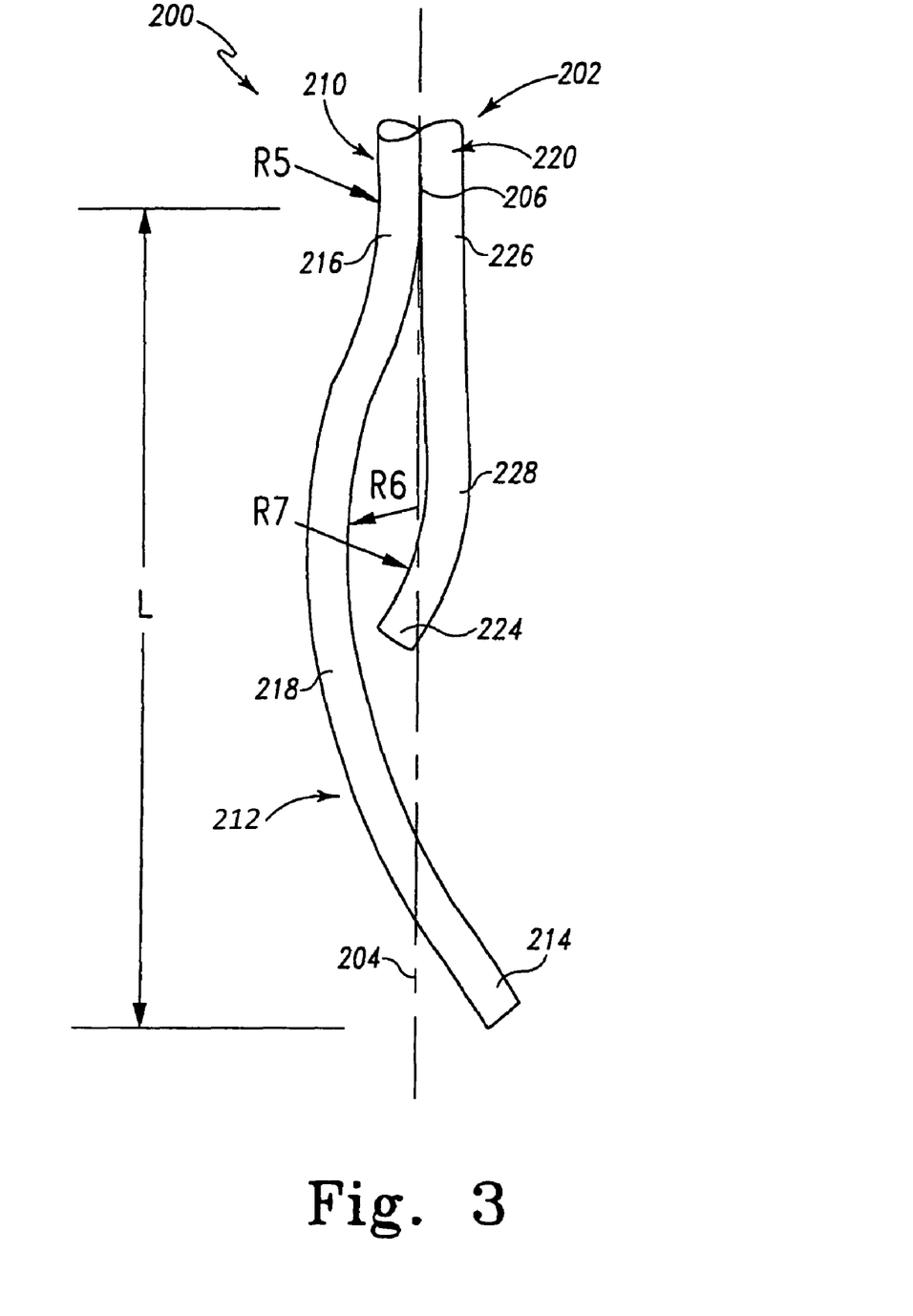
FIG. 3 is a plan view of a distal portion of another embodiment catheter.

FIG. 3 shows another embodiment for a distal portion of a catheter 200 that is similar to catheter 100 discussed above, except lumen part 220 of catheter 200 includes a distal portion with a non-linear profile that includes a single bend. Catheter 200 includes lumen parts 210, 220 extending along longitudinal axis 204. Distal portion 212 extends distally from a bifurcation 206 along a length L, and is implantable in a vascular structure. Length L can be about 6 centimeters, or other suitable length. Lumen parts 210, 220 separate from one another, and lumen part 210 diverges distally from longitudinal axis 204 at bifurcation 206. The portions of lumen parts 210, 220 extending proximally from bifurcation 206 can be coupled together or positioned alongside one another along a proximal portion 202 of catheter 200 in a manner like that discussed for catheter 100. In one embodiment, one of the lumen parts 210,220 can be designated to provide fluid flow to the body of the patient and the other lumen part 210, 220 can be designated to receive fluid flow from the body of the patient. For example, lumen part 210 can provide venous flow and lumen part 220 can provide arterial flow.

Distal end portion 212 forms a double bend along lumen part 210 and a single bend along lumen part 220 to make it less likely that the distal end portion 212 can be encased in a fibrous sheath formed by the patient's body. For example, lumen part 210 forms a first portion 216 that extends from bifurcation 206 along a bend defined by a radius R5. Lumen part 220 forms a first portion 226 that extends linearly along and generally parallels longitudinal axis 204. Radius R5 is located on the side of lumen part 210 away from longitudinal axis 204 so that the lumen parts 210, 220 separate and lumen part 210 diverges distally away from longitudinal axis 204 and lumen part 210 forms a convex relationship toward longitudinal axis 204.

Lumen part 210 also includes a second portion 218 forming a reverse compound curve-like form with first portion 216 that extends along a bend defined by a radius R6 to a distal tip 214. Lumen part 220 also includes a second portion 228 that forms a bend from the linear portion 226 that extends along a bend defined by a radius R7 to a distal tip 224. Radius R6 and radius R7 are located toward longitudinal axis 204 so that the portions 218, 228 are curved away from axis 204 and form a concave relationship oriented toward longitudinal axis 204.

The length of second portion 228 along axis 204 is less than the length of second portion 218 along axis 204 so that the distal tip 224 is spaced proximally of the distal tip 214. The length of second portion 218 and radius R6 is sized so that second portion 218 crosses longitudinal axis 204 from a first side to a second side of longitudinal axis 204 in a transverse relationship, and distal tip 214 is located at least partially on the second side of longitudinal axis 204. The length of second portion 228 and radius R7 is sized so that second portion 228 crosses longitudinal axis 204 from the second side to the first side of longitudinal axis 204 in a transverse relationship, and distal tip 224 is located at least partially on the first side. The radii R5, R6, and R7 are provided as examples of the curvature of the bends of distal portion 212 of the lumen parts 210, 220. The bends of each of the lumen parts 210, 220 can extend along curves formed by multiple radii and that are regular or irregular in form. In another form, the curves include one or more linear or angular segments.

The double bend configuration of distal portion 212 provides a non-linear profile that assists in preventing the formation of a fibrous sheath encasing distal portion 212 when positioned in the patient's body. The diverging and converging relationship between lumen parts 210, 212 provides a non-linear profile for the lumen parts 210, 220 along distal portion 212.

Catheters 100, 200 are provided with the respective distal portions 112, 212 preformed to provide the non-linear profile configurations discussed above. It is further contemplated that one or more wires or other stiffening members can be provided in the wall of the lumen parts 110, 120 or lumen parts 210, 220 to assist in maintaining the preformed non-linear profile configuration prior to implantation and after implantation.

Figures 4, 5:
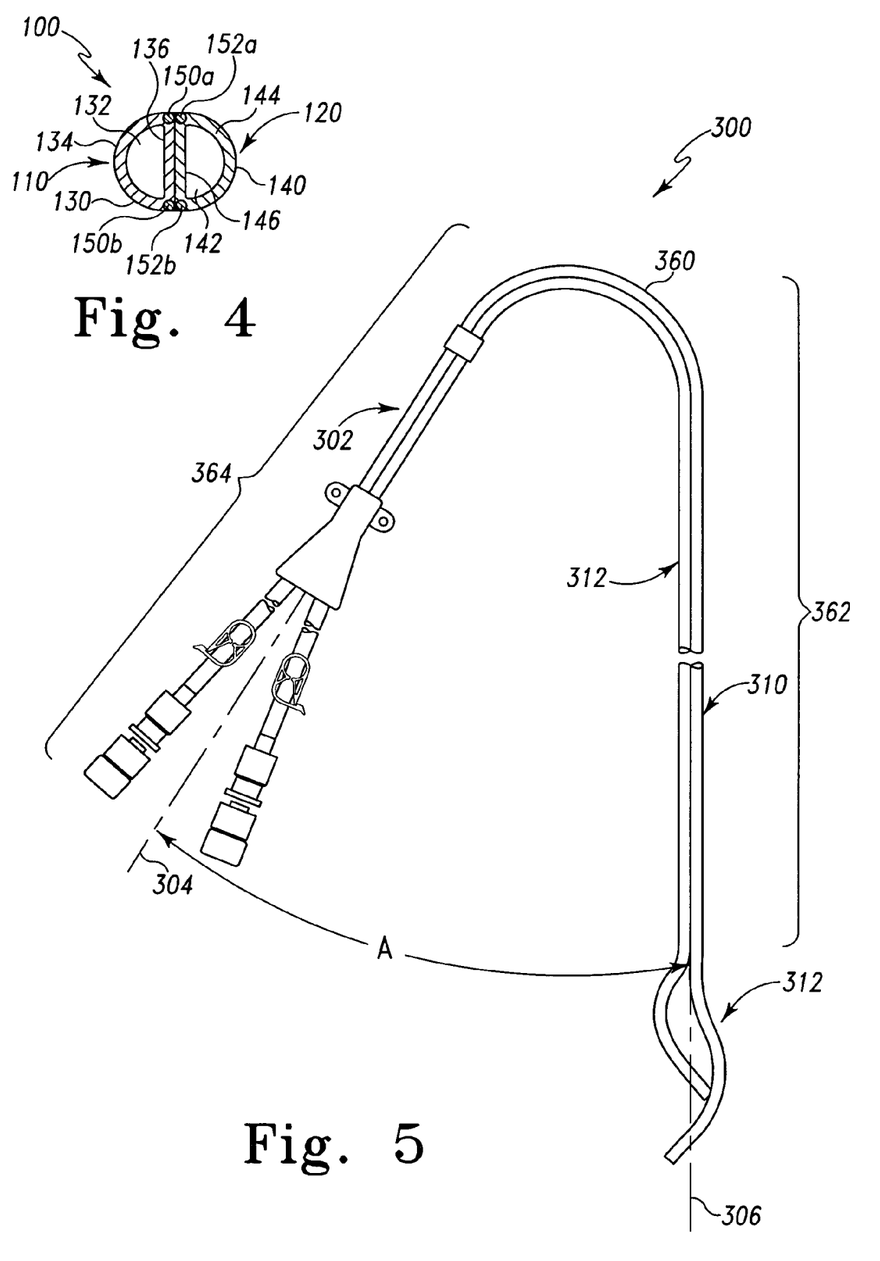
FIG. 4 is a cross-section along line 4-4 of FIG. 1.
FIG. 5 is a plan view of another embodiment catheter.

FIG. 4 is a cross-section through catheter 100 along line 4-4. Lumen part 110 includes a D-shaped wall 130 that defines a central lumen or flow passage 132 extending therethrough. Wall 130 includes an arcuate portion 134, and a linear portion 136 extending between opposite sides of the arcuate portion 134. Similarly, lumen part 120 includes a D-shaped wall 140 that defines a central lumen or flow passage 142 extending therethrough. Wall 140 includes an arcuate portion 144, and a linear portion 146 extending between opposite sides of the arcuate portion 144. Lumen parts 110, 120 are positioned with linear portions 136, 146 in side-by-side relation along longitudinal axis 104, at least proximally of bifurcation 106. Lumen parts 110 can be secured to one another with an adhesive, extrusion technique, fusion, or mechanical fasteners.

Walls 130, 140 also each define a pair of smaller lumens at or adjacent the junction of the respective linear portion 136, 146 with the arcuate portion 134, 144. Wall 130 includes first and second stiffening elements 150a, 150b in these smaller lumens, and wall 140 includes third and fourth stiffening elements 152a, 152b in these smaller lumens. The stiffening elements extend along the length L of at least distal portion 112, and maintain distal portion in its non-linear configuration discussed above. The stiffening elements 150a, 150b and stiffening elements 152a, 152b are elastic so that when the curved configuration along distal portion 112 is straightened as a result of insertion forces or other forces when implanted, the distal portion 112 is biased to return toward the non-linear profile discussed above when the forces are released. In one embodiment, stiffening elements 150a, 150b and stiffening elements 152a, 152b are elongate wires made from shape memory material such as titanium-nickel alloy or spring steel. The stiffening elements can extend along the entire length of the respective lumen part 110, 120, or can extend along only a portion of the length of the respective lumen part 110, 120. In another embodiment, one or both of the lumen parts are provided with a single stiffening element. In yet another embodiment, more than two stiffening elements are provided in the wall of one or both of the lumen parts.

In another embodiment shown in FIG. 5, a catheter 300 is provided that includes a proximal portion 302 and a distal portion 312. Distal portion 312 is illustrated like that of distal portion 112 of catheter 100, it being understood that other distal portion arrangements could also be provided. Proximal portion 302 includes first and second lumen parts 310, 320 that are configured like lumen parts 110, 120 of catheter 100. However, proximal portion 302 includes an intermediate bend 360 that re-orients a distal segment 362 of proximal portion 302 relative to a proximal segment 364 of proximal portion 302.

Proximal segment 364 extends along longitudinal axis 304, and distal segment 362 extends along longitudinal axis 306. Intermediate bend 360 includes a U-shape so that axes 304, 306 define an angle A therebetween. Lumen parts 310, 320 can be pre-formed to include bend 360. Stiffening elements like stiffening elements 150a, 150b and stiffening elements 152a, 152b maintain catheter 300 with bend 360 during packaging and shipment, during the implantation procedure, and after implantation. Bend 360 is curved along a radius to provide a smooth transition between the distal and proximal segments 362, 364 to eliminate or prevent the formation of sharp bends or kinking in the lumen parts 310, 320 that could restrict or prevent flow through the passages thereof.

In one embodiment, angle A is about 30 degrees. Other embodiments contemplate an angle A ranging from 5 degrees to 180 degrees. In yet another embodiment discussed below, bend 360 extends 180 degrees so that the axis 306 of distal segment 362 is parallel to the axis 304 of proximal segment 364.

Referring back to FIG. 1, further details associated with proximal portion 102 of catheter 100 will be discussed, it being understood that the proximal portions of the other catheter embodiments could be arranged similarly to or differently than proximal portion 102. Proximal portion 102 includes a cuff 160 extending around lumen parts 110, 120. Cuff 160 provides a scaffold for tissue ingrowth at the location where catheter 100 enters the skin of the patient. Cuff 160 is polyester felt in one embodiment. Other embodiments contemplate any other suitable structure or material for cuff 160. In other embodiments, cuff 160 is omitted.

Proximal portion 102 of catheter 100 also includes a hub 162 that connects to the proximal ends of the respective lumen parts 110, 120. Hub 162 includes a wing 164 that defines holes for receiving sutures to allow securement of catheter 100 to the patient after implantation. Hub 162 also maintains the separation of passages 132, 142 of lumen parts 110, 120. Passages 132, 142 are in fluid communication with respective ones of the first and second leads 170, 180 extending proximally from hub 162. Leads 170, 180 are also made from flexible tubing, and include female fittings 172, 182, respectively, at their proximal ends. Male fittings 174, 184 are removably engageable to the respectively female fittings 172, 182 to provide a cap to maintain the integrity and sterility of the female fittings 172, 182. Leads 170, 180 also include clamps 176, 186, respectively, that releasably clamp the respective lead 170, 180 to restrict or permit fluid flow through the passages 132, 142 of lumen parts 110, 120.

Various lengths for the catheter 100 are contemplated, it being understood that the other catheter embodiments could also be arranged with the same or with different lengths. Catheter 100 includes a dimension L1 from the distal end of hub 162 to the distal end of lumen part 110. Cuff 160 is spaced a dimension L2 from the distal end of lumen part 110. In one embodiment, dimension L1 ranges from 24 centimeters to 32 centimeters, and dimension L2 ranges from 19 centimeters to 27 centimeters. Catheter 100 includes a dimension L3 from the distal end of hub 162 to the distal end of lumen part 120. Cuff 160 is spaced a dimension L4 from the distal end of lumen part 120. In one embodiment, dimension L3 ranges from 21 centimeters to 29 centimeters, and dimension L4 ranges from 16 centimeters to 24 centimeters. Leads 170, 180 extend proximally from hub 162 along a dimension L5. In one embodiment, dimension L5 is about 3.25 inches. Other embodiments contemplate other dimensions for L1, L2, L3, L4 and L5.

Figure 6:
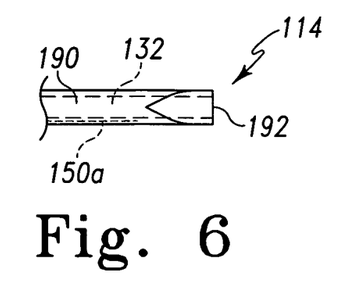
FIG. 6 is a side elevation view of a distal tip of the catheter of FIG. 1.
Figure 7:
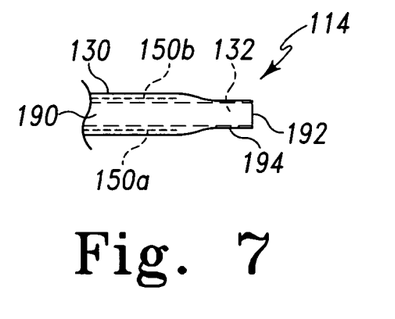
FIG. 7 is a top plan view of the tip of FIG. 6.
Figure 8:
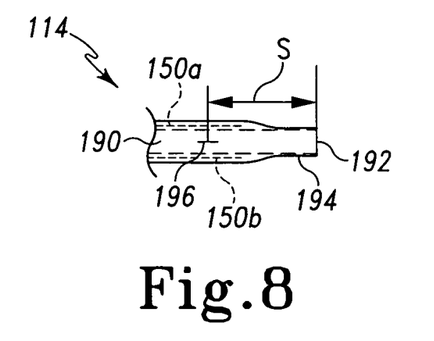
FIG. 8 is a bottom plan view of the tip of FIG. 6.

Various arrangements for the distal tips are contemplated. In one embodiment, the configurations of the respective lumen parts 110, 120 shown in FIG. 4 are carried through the distal tips to provide a distally opening port. In another embodiment, shown in FIGS. 6-8, distal tips 114, 124 include a distally tapered configuration. In FIGS. 6-8, distal tip 114 will be described, it being understood that distal tip 124 could be similarly arranged. Specifically, wall 130 includes a first thickness along a proximal part 190 of tip 114. Stiffening elements 150a, 150b extend in the thickness of wall 130 to a distal end location spaced proximally of distal end 192 of tip 114. The thickness of wall 130 tapers along a distal part 194 of distal tip 114 from the distal end location of stiffening elements 150a, 150b toward distal end 192, where passage 132 opens distally. The cross-section of passage 132 remains constant through distal tip 114 to maximize the area available for flow. The reduced wall thickness along distal part 194 of distal tip 114 increases the flexibility of the distal tip and provides further protection to the vascular structure from trauma should distal tip 114 contact the vessel wall or other anatomic structure.

Distal tip 114 further includes a side port 196 extending along linear wall 136 in the proximal-distal direction. Side port 196 forms an elongated slit that is normally closed, but opens upon application of sufficient fluid pressure to allow at least some fluid flow therethrough. In another embodiment, side port 196 is omitted from distal tip 114. In yet another embodiment, multiple side ports are provided in the distal tip 114.

Figure 9:
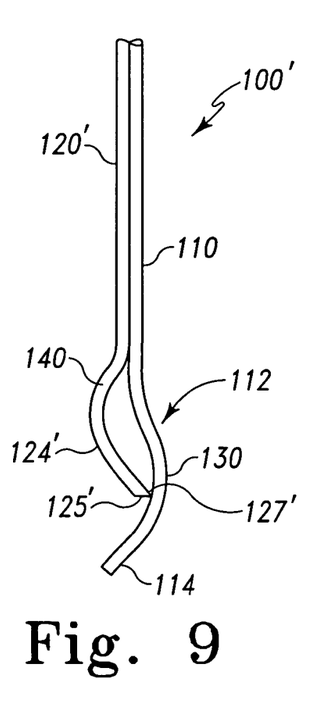
FIG. 9 is a plan view of a distal portion of another embodiment catheter.

In yet another embodiment shown in FIG. 9, a catheter 100' is similar to catheter 100 except for the distal tip of the arterial lumen part 120'. Distal tip 124' is arranged so that the distal opening is oriented in the direction of flow in the vascular structure. Accordingly the distal tip 124' includes a distal end wall 125' that is obliquely oriented to the wall 140 of lumen part 120'. The acutely angled side 127' of distal end wall 125' is positioned toward lumen part 110, and is attached to lumen part 110 to maintain the distal opening oriented in the direction of the fluid flow and away from the vessel wall. The attachment arrangement also prevents the distal opening of distal tip 124' from being obstructed by the wall 130 of lumen part 110 in the vascular structure.

Figure 10:
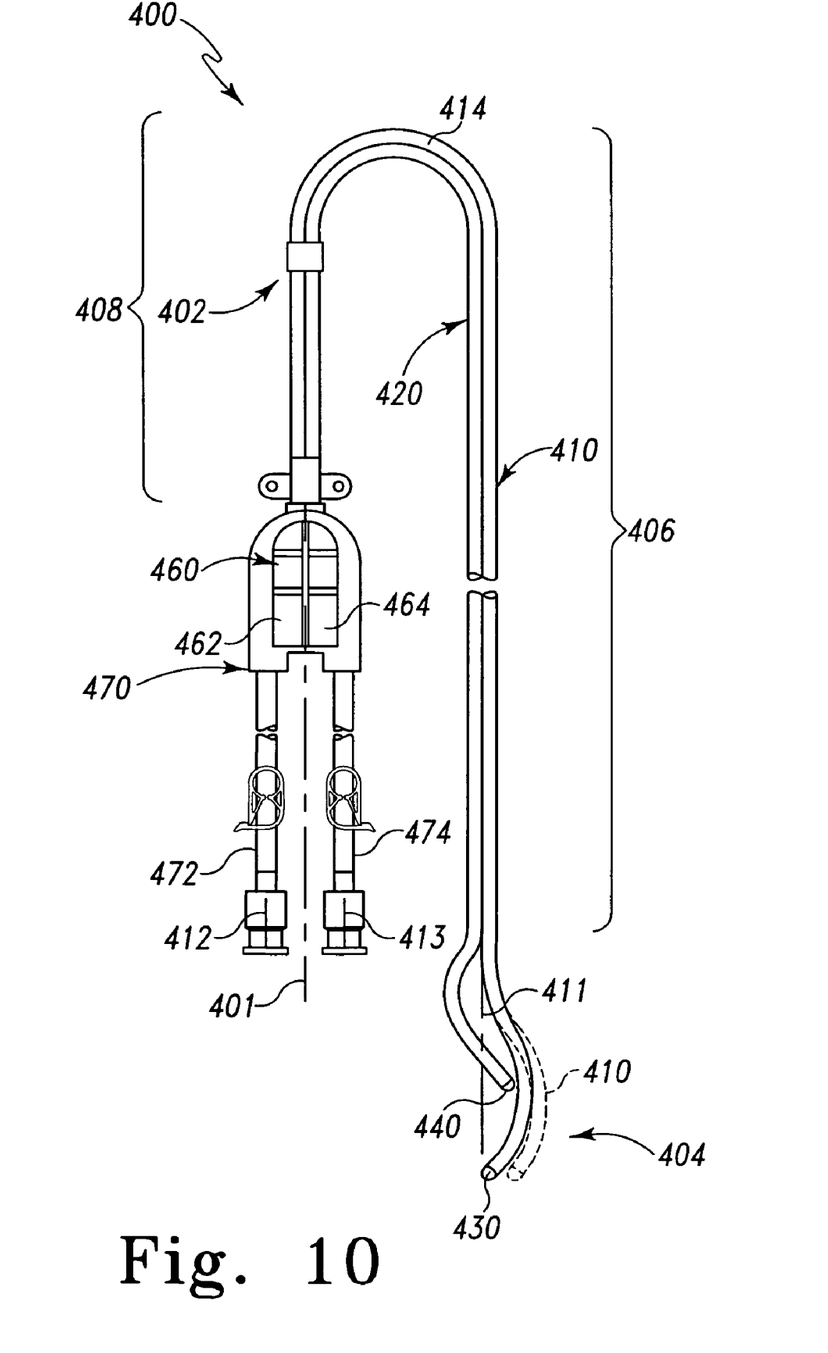
FIG. 10 is a plan view of another embodiment catheter.
Figure 11:
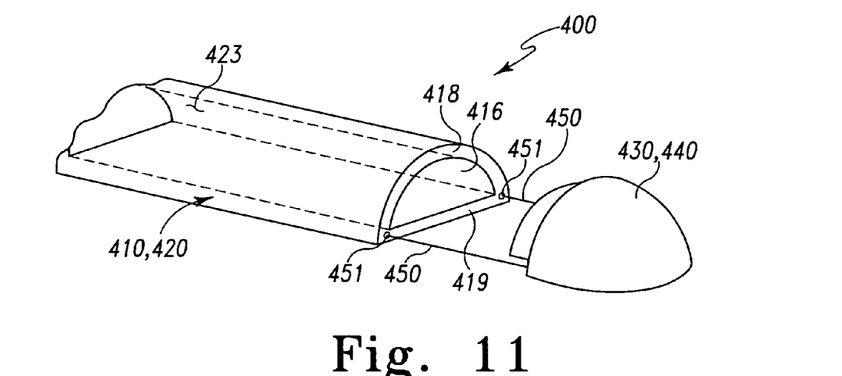
FIG. 11 is a perspective view of a portion of the catheter of FIG. 10 with its port in an open condition.
Figure 12:
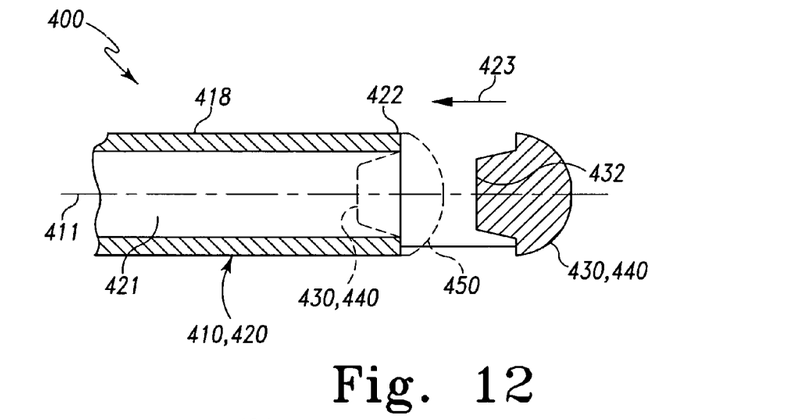
FIG. 12 is a longitudinal section view of the catheter portion in FIG. 11.

FIGS. 10-12 shows another embodiment catheter 400 that is similar to catheter 100, except catheter 400 includes opening and closing mechanisms that are operable with an actuator to selectively open and close the distal ports of the lumen parts. Specifically, catheter 400 includes a first lumen part 410 and a second lumen part 420, and lumen parts 410, 420 form a proximal portion 402 of catheter 400 and a distal portion 404. Lumen parts 410, 420 are substantially identical to lumen parts 110, 120 discussed above, except the stiffening elements are also movable actuating members 450 (FIGS. 11-12) provided in the walls of the lumen parts 410, 420 that are longitudinally movable with actuator 460. Actuator 460 is mounted on a proximal hub 470 that receives the lumen parts 410, 420 and maintains the separate flow paths thereof to leads 472, 474, respectively. Actuating members 450 are coupled to respective ones of the end caps 430, 440 at the distal end of the respective lumen parts 410, 420 and are movable longitudinally to open and close the distal port with the respective end cap 430, 440. Actuating members 450 also provide a stiffening element like the stiffening elements 150a, 150b, 152a, 152b discussed above to maintain the shape of the lumen parts 410, 420 and the non-linear profile along distal portion 404.

Proximal portion 402 includes a distal segment 406 extending along longitudinal axis 411 and proximal segment 408 extending along longitudinal axis 401. Proximal segment 408 is connected with distal segment 406 with a 180 degree bend 414 so that longitudinal axes 401, 411 are parallel to one another. Other embodiments contemplate other angular arrangements between axes 401, 411 as discussed above with respect to catheters 100 and 300.

In FIGS. 11-12 there is shown one lumen part 410, 420 at distal portion 404 of catheter 400, it being understood that the lumen parts 410, 420 are identical to lumen parts 110, 120 discussed above except as otherwise discussed herein. Lumen parts 410, 420 each include a body formed by a wall 418 extending about a lumen or passage 421 that provides for fluid flow through the lumen part. Lumen 421 opens at a distal end 422 of lumen parts 410, 420 to form a distally opening port 416 for ingress and/or egress of fluid flow.

In addition, catheter 400 includes end caps 430, 440 associated with each respective lumen part 410, 420. End caps 430, 440 are movable relative to the distal end of lumen part 410, 420 from an open position, as shown in FIG. 11, to a closed position by manipulating the actuating members 450. The port 416 can be opened by deforming catheter 400 from its closed position by displacing end cap 430, 440 distally from its closed position to the open position. In the open position, cap 430, 440 is spaced from distal end 422, resulting in a change of length of catheter 400, so that port 416 is open to permit fluid passage from or into lumen 421. End caps 430, 440 are coupled to lumen parts 410, 420 with one or more actuating members 450 that extend between lumen parts 410, 420 and end caps 430, 440. Actuating members 450 are in the form of an actuating wire in wall 418 at or adjacent the junction of the linear portion 419 and the rounded, convex portion 423. Each actuating member 450 is positioned in a lumen 451 formed in wall 418 along the length of the respective lumen part 410, 420. Such a lumen 451 for receiving the respective actuating member 450 could be formed by a flat wire coil of stainless steel or shape memory material. Actuating members 450 can also be made from stainless steel, shape memory material, or any suitable material. Actuating members 450 and one or more other actuating members or non-movable stiffening elements can be located at other locations about wall 418.

End caps 430, 440 can be moved to the closed position from the open position by axially and proximally displacing end caps 430, 440 toward port 416 along longitudinal axis 411 and into sealing engagement with the respective lumen part 410, 420. Actuating members 450 are coupled to an actuating mechanism to allow displacement of the actuating members 450, and thus the end caps 430, 440 coupled thereto, proximally along axis 411 to the closed position, as indicated in dashed lines in FIG. 12. To open port 416, actuating members 450 are displaced distally with the actuator mechanism to displace cap 430, 440 distally along axis 411 and relative to port 416 of the respective lumen part 410, 420. End caps 430, 440 include a tapered proximal portion 432 that can facilitate receipt through port 416 into lumen 421. The tapered portion 432 can also allow end caps 430, 440 to self-center relative to port 416 and provide sealing engagement with wall 418 of the respective lumen part 410, 420. In another embodiment, end caps 430, 440 are configured with a receptacle that receives the end of the respective lumen part therein in the closed position.

Referring back to FIG. 10, when end cap 440 of lumen part 420 is opened, it contacts lumen part 410 at distal portion 404 and displaces it away from longitudinal axis 411, as shown in dashed lines. This in turn can free up or loosen any fibrous sheath formed along the lumen parts 410, 420. Furthermore, opening and closing of the caps 430, 440 frees or loosens any fibrous sheath formed on the distal portions of the lumen parts 410, 420. Furthermore, the non-linear orientation of lumen parts 410, 420 and the movable port structures provided thereon can run along lumen part 410 during opening and closing of the port, displacing and mitigating any build-up of a fibrous sheath. The transverse orientation of the distal tips of lumen parts 410, 420 to longitudinal axis 411 orients the ports in a transverse relationship to the vasculature structure while the end caps 430, 440 displace the ports from the vasculature structures if in contact therewith and prevents or mitigates blockage of flow from the ports by the vascular structure in which the distal tips are positioned.

FIG. 10 further shows lumen parts 410, 420 coupled together at proximal hub 470. Proximal hub 470 includes a configuration that separates the two lumen parts 410, 420 for connection with leads 472, 474, which can be configured like leads 170, 180 discussed above for catheter 100. In one embodiment, one of the lumen parts 410, 420 can be designated to provide fluid flow to the body of the patient and the other lumen part 410, 420 can be designated to receive fluid flow from the body of the patient, as indicated by arrows 412, 413.

Actuator 460 includes first and second slide buttons 462, 464 associated with respective ones of the first and second lumen parts 410, 420 that are mounted or coupled to hub 470. Slide buttons 462, 464 are longitudinally moveable to move one or more actuating members 450 engaged therewith to open and close a respective one of the end caps 430, 440. Slide buttons 462, 464 allow for remote manipulation of the movement of the actuating members 450 and the associate end cap 430, 440 of the respective lumen part 410, 420 along the wall of the lumen part. The separated slide buttons 462, 464 can be moved axially in either the proximal or distal directions, as desired, to effect corresponding independent and remotely activated movement of the end caps 430, 440, depending on the lumen part 410, 420 manipulated with actuator 460. Such movement allows selective opening and closing of the one or more ports to allow fluid flow therethrough.

Figure 13:
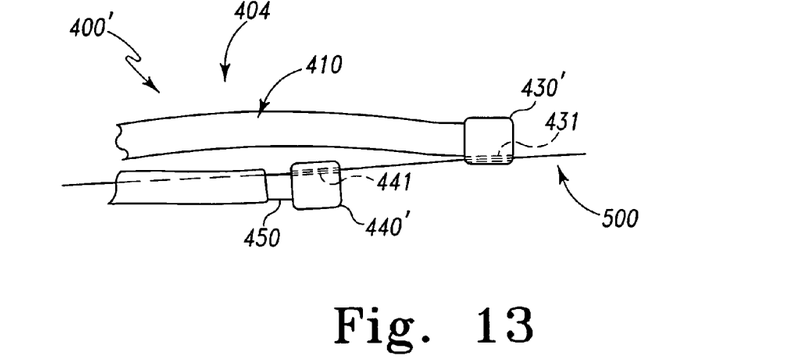
FIG. 13 is a plan view of a distal portion of another embodiment catheter and a guidewire.

In FIG. 13 there is shown another embodiment of distal portion 402 of catheter 400, designated as catheter 400'. Catheter 400' includes lumen parts 410, 420 but another embodiment end cap 430', 440' associated with the respective lumen parts 410, 420. End caps 430', 440' are coupled to the lumen parts with actuating members 450, but include passages 431, 441, respectively, to receive a guidewire 500 to facilitate percutaneous placement of the catheter 400 into the patient.

In use, guide wire 500 is positioned to the catheter implantation location in the patient. Caps 430', 440' are moved to the closed position, and the proximal end of guidewire 500 is threaded through longitudinal passage 431 of end cap 430'. End cap 440' is then opened and the proximal end of guidewire 500 is positioned through passage 421 through the proximal end of lumen part 420. Alternatively, guidewire 500 is positioned through a passage 441 extending longitudinally through end cap 440'. Catheter 400' is then guided along the guidewire 500 to locate the distal ends of lumen parts 410, 420 at the implantation location.

In one procedure employing the catheters discussed herein, the distal end of the longer or venous lumen part is positioned in the right atrium of the heart, and the distal end of the shorter or arterial lumen part is positioned at the junction of the superior vena cava and the right atrium. Other procedures contemplate other implantation locations and techniques. For example, catheter 100 can be positioned to the implantation location by positioning the guidewire through the passage of one of the lumen parts 110, 120 and guiding the catheter 100 along the guidewire to the implantation location. The distal portion of the catheter at the bifurcation can be held together with a releasable band or suture to facilitate insertion. In another procedure, the distal ends of any of the catheter embodiments are positioned in a tunneling device to maintain the non-linear distal portion in a more linear configuration. The catheter is inserted into the patient in the more linear configuration, and released from the tunneling device after implantation to return toward the non-linear profile along the distal portion. In any procedure, the positioning and placement of the catheters can be monitored with ultrasound and fluoroscopy.

While the invention has been illustrated and described in detail in the drawings and foregoing description, the same is to be considered as illustrative and not restrictive in character. For example, for any embodiment catheter actuating mechanisms are contemplated that include micro-motors or other automatic or mechanical systems for opening and closing the fluid flow ports. All changes and modifications that come within the spirit of the invention are desired to be protected.

What is claimed is:

1. A catheter, comprising:
   a first lumen part and a second lumen part extending along a longitudinal axis in side-by-side relation, said first and second lumen parts forming a proximal portion and a distal portion of the catheter, wherein at least a distal segment of said proximal portion extends along said longitudinal axis and said first and second lumen parts separate from one another at a bifurcation between said distal and proximal portions, wherein said longitudinal axis passes through said bifurcation, wherein said first lumen part extends distally from said bifurcation and includes a first bend so that said first lumen part is concavely curved toward said longitudinal axis on a first side of said longitudinal axis, wherein said second lumen part extends distally from said bifurcation and includes a second bend so that said second lumen part is concavely curved toward said longitudinal axis on a second side of said longitudinal axis such that a linear extension of said second lumen part at said distal end thereof would intersect at least a portion of said first lumen part, wherein each of said first and second bends includes an apex point that is the point of each lumen part that is most distant from said longitudinal axis, wherein said apex of said first lumen part is spaced distally along the longitudinal axis of the apex of the second lumen part, wherein said first lumen part includes a first opening spaced distally along the longitudinal axis of a second opening at a distal end of said second lumen part, wherein at least one of said first lumen part and said second lumen part includes a non-linear configuration extending from said bifurcation to a distal end thereof, and wherein said distal portion of said second lumen part is unattached to said distal portion of said first lumen part.

2. The catheter of claim 1, wherein said first lumen part and said second lumen part each include a D-shaped wall along said proximal and distal portions, each of said D-shaped walls defining a central passage extending along said respective lumen part.

3. The catheter of claim 2, wherein said first and second lumen parts each include a pair of elongated stiffening elements in said wall, said elongated stiffening elements extending along said proximal and distal portions of the catheter.

4. The catheter of claim 3, wherein said first and second openings are positioned at said distal end of said first and second lumen parts, and further comprising a cap at said distal end of each of said first and second lumen parts, wherein said stiffening elements are coupled to a respective one of said caps and are movable in said wall of said respective lumen part to move said respective cap from an open position spaced from said distal end of said respective lumen part to a closed position engaged to said distal end of said respective lumen part to close said passage thereof.

5. The catheter of claim 4, wherein said stiffening elements of each of said first and second lumen parts are coupled with an actuator adjacent a proximal end of said first and second lumen parts, said actuator being operable to selectively move each of said caps between said open and closed positions.

6. The catheter of claim 1, wherein said first lumen part is curved so that said distal end thereof is located on said second side of said longitudinal axis.

7. The catheter of claim 6, wherein said second lumen part is curved so that said distal end thereof is located on said first side of said longitudinal axis.

8. The catheter of claim 1, wherein said first lumen part has a length along said longitudinal axis that is greater than a length of said second lumen part along said longitudinal axis so that said distal end of said first lumen part is spaced distally of said distal end of said second lumen part along said longitudinal axis.

9. The catheter of claim 1, wherein said proximal portion of said first and second lumen parts includes a proximal segment extending along a second longitudinal axis and a bend connecting said proximal segment and said distal segment, wherein said longitudinal axes form an angle of about 30 degrees.

10. The catheter of claim 1, wherein said proximal portion of said first and second lumen parts includes a proximal segment extending along a second longitudinal axis and a bend connecting said proximal segment and said distal segment, wherein said longitudinal axes are parallel to one another.

11. The catheter of claim 1, wherein:
   said first lumen part forms a third bend at said bifurcation and said first bend is distal of said third bend, said first and third bends forming a reverse compound curve along said first lumen part; and
   said second lumen part forms a fourth bend at said bifurcation and said second bend is distal of said fourth bend, said second and fourth bends forming a reverse compound curve along said second lumen part.

12. The catheter of claim 1, wherein at least one of said first and second lumen parts includes a distal tip and said distal tip includes a proximal part with a first wall thickness and at least one stiffening element extending in said first wall thickness, said at least one stiffening element terminating in said proximal part and said distal tip including a distal part and said wall thickness tapers distally from said proximal part along said distal part to a distal end of said distal tip.

13. The catheter of claim 1 wherein said first lumen part includes a first distal end portion adjacent to said distal end of said first lumen part, said first distal end portion extending obliquely to said longitudinal axis.

14. The catheter of claim 1 wherein said second lumen part includes a second distal end portion adjacent to said distal end of said second lumen part, said second distal end portion extending obliquely to said longitudinal axis.

15. A catheter, comprising:

a first lumen part and a second lumen part extending in side-by-side relation, said first and second lumen parts forming a proximal portion and a distal portion of the catheter, wherein at least a distal segment of said proximal portion extends along a longitudinal axis and said first and second lumen parts separate from one another at a bifurcation between said distal and proximal portions, wherein said longitudinal axis passes through said bifurcation, wherein said first lumen part extends distally from said bifurcation and includes a first bend so that said first lumen part is concavely curved relative to said longitudinal axis on a first side of said longitudinal axis and converges distally toward the longitudinal axis, and wherein said second lumen part extends distally from said bifurcation and includes a second bend so that said second lumen part is concavely curved relative to said longitudinal axis on a second side of said longitudinal axis and converges distally toward the longitudinal axis, wherein each of said first and second bends includes an apex point that is the point of each lumen part that is most distant from said longitudinal axis, wherein said apex of said first lumen part is spaced distally along the longitudinal axis of the apex of the second lumen part, wherein said first lumen part includes a first opening at a distal end of said first lumen part, and spaced distally along the longitudinal axis of a second opening at a distal end of said second lumen part; wherein said second lumen part extends independently of said first lumen part from said bifurcation to said distal end of said second lumen part, and wherein said second lumen part is oriented such that a linear extension of said second lumen part at said distal end thereof would intersect at least a portion of said first lumen part.

* * * * *